United States Patent [19]
Milam et al.

[11] Patent Number: 5,668,075
[45] Date of Patent: Sep. 16, 1997

[54] RESTRUCTURED IRON OXIDE FOR USE IN IRON OXIDE CATALYSTS

[75] Inventors: Stanley Nemec Milam, Spring; Brent Howard Shanks, Houston, both of Tex.

[73] Assignee: Shell Oil Company, Houston, Tex.

[21] Appl. No.: 644,694

[22] Filed: May 10, 1996

Related U.S. Application Data

[63] Continuation of Ser. No. 356,024, Dec. 14, 1994, abandoned.
[51] Int. Cl.$^6$ .............................. B01J 23/70; C01G 49/02
[52] U.S. Cl. ............................................ 502/338; 423/632
[58] Field of Search ........................... 423/632; 502/338, 502/326, 331; 585/444, 661

[56] References Cited

U.S. PATENT DOCUMENTS

| | | |
|---|---|---|
| 3,904,552 | 9/1975 | O'Hara . |
| 4,006,090 | 2/1977 | Beck . |
| 4,052,338 | 10/1977 | Riesser . |
| 4,098,723 | 7/1978 | Riesser . |
| 4,143,083 | 3/1979 | Riesser . |
| 4,144,197 | 3/1979 | Riesser . |
| 4,152,300 | 5/1979 | Riesser . |
| 4,749,674 | 7/1988 | Dejaifve et al. . |
| 4,857,498 | 8/1989 | Dejaifve et al. . |
| 4,975,407 | 12/1990 | Dejaifve et al. . |
| 5,023,225 | 7/1991 | Williams et al. . |
| 5,093,100 | 3/1992 | Sadamura et al. ............... 423/632 |
| 5,171,914 | 12/1992 | Hamilton, Jr. . |

FOREIGN PATENT DOCUMENTS

| | | | |
|---|---|---|---|
| 13520 | 11/1966 | Australia . | |
| 693822 | 9/1964 | Canada | ............................... 585/444 |

OTHER PUBLICATIONS

Nicholas J. Reeves and Stephen Mann, Influence of Inorganic and Organic Additives on the Tailored Synthesis of Iron Oxides, pp. 3875–3880, no date.

Kenneth R. Hancock, Mineral Pigments, pp. 349–372, no date.

M. Muhler, R. Schlogl, and G. Ertl, The Nature of the Iron Oxide-Based Catalyst for Dehydrogenation of Ethylbenzene to Styrene, Journal of Catalysis, 138, pp. 413–444, 1992.

Jianmin Zhao et al., Role of Molybdenum at the Iron Oxide Surface, Journal of Catalysis 148, pp. 194–197, 1994.

Wang, et al., Nonoxidative Dehydration of Ethylbenzene Over $TiO_2$–$ZrO_2$ Catalysts, Journal of Catalysis 83, pp. 428–436, 1983, no month.

Min–Dar Lee et al., Effects of Addition of Chromium, Manganese, or Molybdenum to Iron Catalysts for Carbon Dioxide Hydrogenation, Applied Catalysis, 72, pp. 267–281, 1991, no month.

G. A. Smorjai, Modern Concepts in Surface Science and Heterogeneous Catalysis, J. Phys. Chem., pp. 1013–1023, 1990, no month.

Primary Examiner—Steven Bos
Attorney, Agent, or Firm—Todd F. Volyn

[57] ABSTRACT

In one aspect of the invention, a composition is presented comprising restructured iron oxide particles. A method is also presented for restructuring iron oxide particles to form low surface area iron oxide particles. In this method, iron oxide particles are contacted with an effective mount of a restructuring agent and are then heated until restructuring occurs.

8 Claims, 6 Drawing Sheets

5,668,075

RESTRUCTURED IRON OXIDE FOR USE IN IRON OXIDE CATALYSTS

This is a continuation of application Ser. No. 08/356,024 filed Dec. 14, 1994, now abandoned.

FIELD OF THE INVENTION

This invention is related to iron oxide and catalysis.

BACKGROUND OF THE INVENTION

Iron oxide materials exist naturally as several minerals. These minerals include red, yellow, brown, and black iron oxide materials. For example, red iron oxide minerals are usually hematite ($\alpha$-$Fe_2O_3$) which has a hexagonal crystal system and occurs in several well known habits. Yellow iron oxide can be lepidocrocite ($\gamma$-FeOOH or $Fe_2O_3.nH_2O$) or goethite ($\alpha$-FeOOH or $Fe_2O_3.nH_2O$) which have an orthorhombic crystal class and may occur in a variety of habits. Brown iron oxide is maghemite ($\gamma$-$Fe_2O_3$) which is dimorphous with hematite. Black iron oxide is magnetite ($Fe_3O_4$) which has a cubic crystal system and may also be found in a number of habits. Brown and black iron oxide are often magnetic.

Iron oxide is an important component in pigments, catalysts, magnetic recording and storage media, and many other applications. While much work has been done in the development of these applications, determining which parameters of a given iron oxide material are responsible for a given characteristic making it desirable for that particular application is not readily amenable to theoretical treatment. It is known that the shape, size, and crystal structure of the particles formed by iron oxide are important or even determinative of their properties. However, the precise nature of the relationship among these characteristics and their resulting properties is most often established empirically.

Synthetic hematite, goethite, lepidocrocite, and magnetite are among the most important iron oxides for use in industrial applications. Synthetic hematite produced by calcination of synthetic goethite is most widely used to catalyze the conversion of ethylbenzene to styrene because these materials often have the highest purity (>98%$Fe_2O_3$).

Synthetic hematite may take on several different particle habits depending upon the process in which it was made. Acicular (needle shaped) synthetic hematite particles may be obtained by calcination of yellow iron oxide produced by the Laux process for aniline manufacture. Branched acicular particles may be obtained by calcination of synthetically produced goethite. Random spheroidal synthetic hematite may be obtained from the Ruthner process for regeneration of spent steel mill "pickling" acid. Synthetic cubic hematite particles may be obtained by calcination of synthetic magnetite.

Certain catalytic substances can undergo significant changes in surface structure under differing conditions. This can have a profound impact on the electronic and chemical properties of the substances including their catalytic activity. For example, some such changes can be adsorbate induced and such changes are largely directed to forming a more thermodynamically stable adsorbate-surface configuration. Typically, such restructuring of the surface occurs in cluster-like fashion. That is, the effect is largely localized on the surface to which the adsorbate adheres. It is also known that certain substances can be used to modify the structure of a catalyst or promote its selectivity or activity. An example of this is found in the addition of alumina to iron catalysts for use in the catalytic synthesis of ammonia. The addition of alumina probably results in a restructuring of the iron compound which is likely a chemical effect due to the formation of an iron aluminate.

U.S. Pat. Nos. 4,052,338; 4,098,723; 4,143,083; 4,144,197; and 4,152,300 all propose dehydrogenation catalysts comprising small amounts of oxidic compounds and rare earths added to iron-potassium oxide base catalysts. In each case, these components were blended, pelletized, and dried. The pellets were then calcined. Selectivity was consistent at approximately 92 mole % (for styrene) among these compositions at a 70% molar conversion of ethylbenzene to products.

It has now been found that iron oxide compositions can be restructured to prepare particles with low surface area and uniquely modified habits. They are particularly useful as catalysts. Catalysts comprised of these compositions have enhanced selectivity in the reactions they are used to catalyze.

SUMMARY OF THE INVENTION

In one aspect of the invention, a composition is presented comprising iron oxide particles having lengths of about 0.3 to about 3 μm, widths of about 0.2 to about 2 μm, and surface area of less than about 1.9 meters squared per gram ($m^2/g$).

These particles are formed by restructuring spheroidal, cubic, acicular or branched acicular iron oxide particles.

In another aspect of the invention, this composition comprises an effective amount of a restructuring agent.

In yet another aspect of this invention, the restructuring agent comprises a substance including an element selected from the group consisting of Be, Mg, Ca, Sr, Ba, Sc, Y, La, Ti, Zr, Hf, V, Nb, Ta, Cr, Mo, W, Mn, Tc, Re, Ru, Os, Co, Rh, Ir, Ni, Pd, Pt, Cu, Ag, Au, Zn, Cd, Hg, Al, Ga, In, Tl, Ge, Sn, Sb, Bi, Ce, Pr, Nd, Pm, Sm, Eu, Gd, Tb, Dy, Ho, Er, Tm, Yb, and Lu.

In another aspect of this invention, a method is presented for restructuring iron oxide particles comprising contacting iron oxide particles with an effective amount of a restructuring agent, heating the iron oxide particles in contact with the restructuring agent to the restructuring point and allowing the restructured iron oxide particles to cool.

In yet another aspect of this invention subsequent treatment with, for example, catalyst modifiers or promoters is performed.

DETAILED DESCRIPTION

It has now been found that iron oxide particles restructured to low surface area and essentially equant habits can be used to prepare dehydrogenation catalysts with enhanced selectivities with respect to those found in the art. Iron oxide can be deliberately restructured for this purpose. These new iron oxide compositions are particularly useful in the dehydrogenation of compounds having the general formula: $R_1R_2CHCH_3$ to form compounds having the formula $R_1R_2CCH_2$ wherein $R_1$ and $R_2$ each represent an alkyl, alkenyl, aryl group (such as a phenyl group) or a hydrogen atom.

The compositions of this invention comprise preferred catalysts in the production of styrene from ethylbenzene and the in the production of alpha-methyl-styrene from cumene. Catalysts prepared from the compositions of this invention also find utility in the dehydrogenation of many substances having carbon-carbon double bonds.

Habit, as used throughout this specification, refers to particle external shape. In contrast, crystal system refers to the internal repeating geometric arrangement of atoms. A material with a single crystal structure can have many different habits depending upon crystal preparation (or growth) conditions. For example, when one refers to a material as acicular they are referring to its habit. When one refers to that same material as having a hexagonal structure they are referring to its crystal system. Control of the crystallization rate and conditions present during crystal growth are ways of affecting habit.

Equant, as used throughout this specification, refers to the shape of an object or particle whose length, breadth, and depth are equal (the aspect ratio is 1). As used throughout this specification, essentially equant refers to the shape of an object or particle whose length, breadth, and depth are similar but are not necessarily equal. As used throughout this specification, the aspect ratio of a particle or object is the ratio of its length to its breadth. The essentially equant iron oxide particles of this invention may also have essentially equant appendages.

Figure 2:
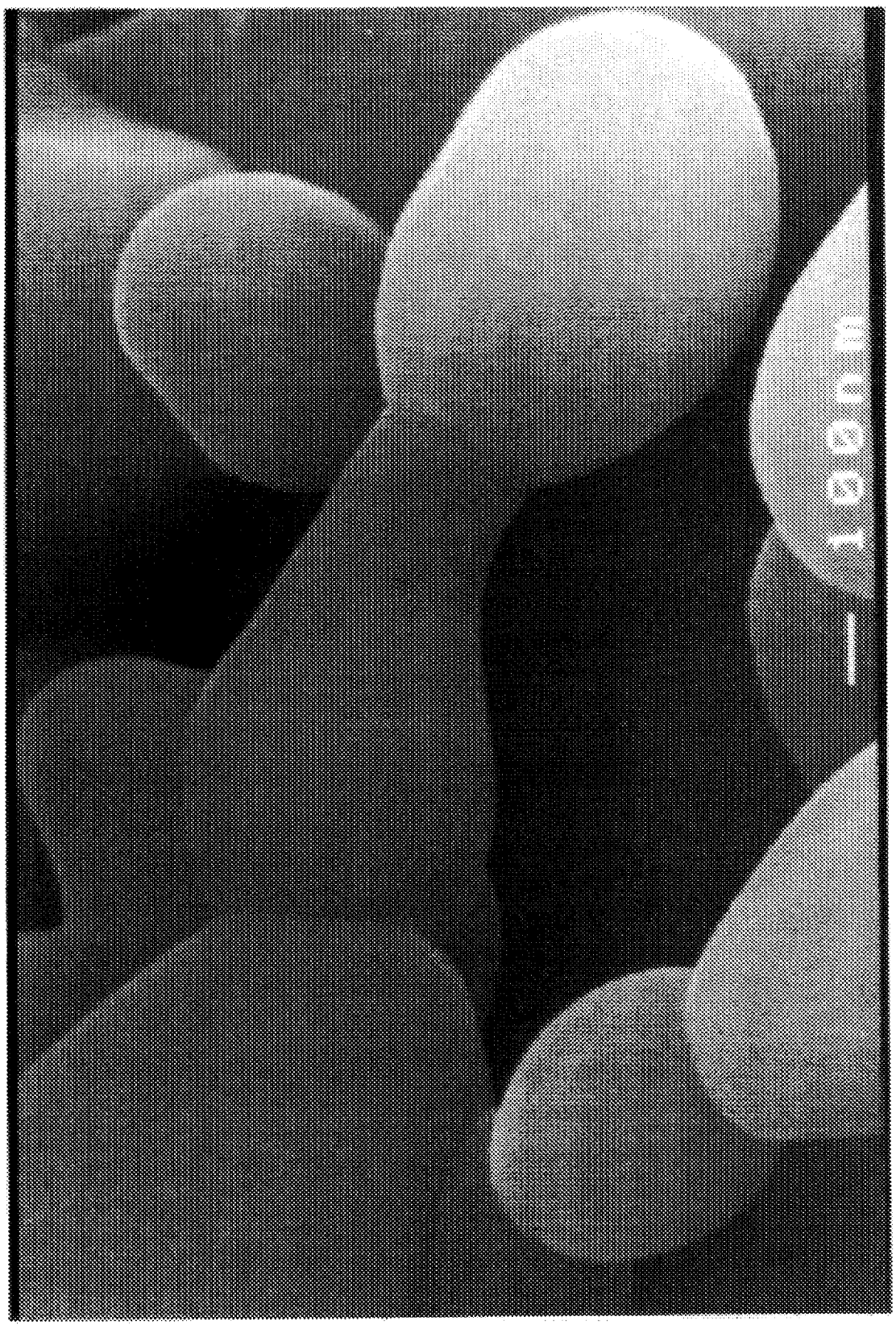
FIG. 2 is a scanning electron micrograph (50,000×) of the low surface area essentially equant iron oxide particles of this invention formed by restructuring red branched acicular iron oxide with copper oxide.

The particles of this invention can also appear as aggregates or agglomerates. One particle can be distinguished from another particle by the presence of an interfacial joint that often appears as a plane in, for example, electron micrographs. The structures on either side of the interfacial joint are thus considered individual particles. FIG. 2 shows this aspect of the restructured iron oxide particles. Observation reveals that a separate particle is found on each side of the interfacial joint.

The restructured iron oxide material of this invention is comprised of particles having lengths of about 0.3 to about 3 μm and breadth of about 0.2 to about 2 μm. The surface area of the compositions of this invention have thus far been found to be less than about 1.9 meters squared per gram ($m^2/g$).

The iron oxide to be restructured may be, for example, hydrated or non-hydrated $Fe_2O_3$ or precursors thereto whether synthetically produced or naturally found. Spheroidal, cubic, acicular or branched acicular synthetic hematite with purity exceeding 98% by weight is preferred. Several commercial manufacturers of synthetic hematite having such particle habits are known in the art; synthetic hematite (red iron oxide) from those suppliers may be used to produce the restructured iron oxide of this invention. Alternatively, iron oxide compositions derived from natural sources may also be acceptable.

Acicular or branched acicular iron oxide is restructured to form essentially equant iron oxide over a range of conditions and parameters. In the broadest sense, the restructuring has occurred when the particle surface area is reduced with respect to the iron oxide starting materials to less than about 1.9 meters squared per gram ($m^2/g$). It is preferred that surface areas are reduced to less than about 1.5 $m^2/g$. It is most preferred that surface areas are reduced to less than about 1.2 $m^2/g$. Restructuring is also accompanied by a changes in particle length and/or breadth. Preferred particles are restructured so that they have lengths between about 0.3 and 3 μm and breadths between about 0.2 and 2 μm. Restructuring is sometimes accompanied by the formation of well defined particle edges and the agglomeration of neighboring particles.

Synthetic spheroidal or cubic iron oxide starting materials are more equant than acicular or branched acicular iron oxides by virtue of the processes by which they were prepared. Nonetheless, these iron oxides may be restructured in much the same way that acicular and branched acicular iron oxides are restructured. Indeed, restructuring has occurred when the above specified physical parameters have been attained.

Restructuring conditions also include heating the iron oxide starting material in the presence of a restructuring agent. This can be followed by relaxation or cooling. Heating the iron oxide starting materials is done by exposing it to, or adding to it, energy well beyond that which the substance ordinarily encounters under ambient conditions. This can be done, for example, by heating the iron oxide through any number of means. Heating cannot exceed the melting point of iron oxide, which is about 1600° C. Generally, however, temperatures in excess of 600° C. have been found effective in forming particles with the new particle size and reduced surface area.

Restructuring also requires the presence of an agent which when combined with a particle capable of undergoing restructuring, such as red iron oxide, helps promote the change in physical parameters. In this specification, such a substance is referred to as a restructuring agent. Thus far, it has been found that between about 0.5% wt and 6% wt of restructuring agent (basis total weight of restructuring agent and iron oxide) will result in restructuring of iron oxide upon heating as set forth above. However, the specific amount of restructuring agent used is not perceived to be critical to this invention. Not wishing to be bound to theory, it is believed that the restructuring agent behaves in a catalytic way; reducing the energy of activation for the restructuring process. Thus, greater or lesser quantities of restructuring agent than those mentioned above will also enhance the restructuring process albeit to a variable degree.

The restructuring agent comprises a substance including an element selected from the group consisting of Be, Mg, Ca, Sr, Ba, So, Y, La, Ti, Zr, Hf, V, Nb, Ta, Cr, Mo, W, Mn, Tc, Re, Ru, Os, Co, Rh, Ir, Ni, Pd, Pt, Cu, Ag, Au, Zn, Cd, Hg, Al, Ga, In, Tl, Ge, Sn, Sb, Bi, Ce, Pr, Nd, Pm, Sm, Eu, Gd, Tb, Dy, Ho, Er, Tm, Yb, and Lu. Such substances can include, for example monometallic oxidic salts such as ammonium dimolybdate; bimetallic oxidic salts such as potassium permanganate; hydroxidic salts such as lanthanum hydroxide; simple salts such as cerium (III) carbonate and magnesium nitrate; oxides such as copper oxide; carbon containing compounds such as calcium acetate; mixtures thereof and hydrates or solvates thereof. Preferred restructuring agents are compounds and/or salts of molybdenum, copper, calcium, zinc, cobalt, and cerium. The most preferred restructuring agents are ammonium dimolybdate, molybdenum trioxide, copper oxide, zinc oxide, calcium acetate, cobalt carbonate, and cerium (III) carbonate.

The application of energy/heat over time periods between about 10 minutes and 3 hours at the restructuring temperature has been found to be effective. Nonhomogeneous restructuring can result when the heating/energizing time is too short. Beyond about 4 hours at a given temperature little additional restructuring generally occurs. Restructuring generally occurs over a range of times at a given temperature. The restructuring rate is faster at higher temperatures. The preferred combination of time and temperature for heating iron oxide in the presence of a restructuring agent in order to bring about restructuring is about one hour at between about 800° and 1100° C. The most preferred parameters of the combination of time and temperature used to bring about restructuring for a given restructuring agent is set forth in Table 1:

TABLE 1

| RESTRUCTURING AGENT | TIME (MINUTES) | TEMPERATURE (°C.) |
| --- | --- | --- |
| Ammonium Dimolybdate | 60 | 800–900 |
| Molybdenum Trioxide | 60 | 800–900 |
| Copper Oxide | 60 | 900–1100 |
| Calcium Acetate | 60 | 900–1100 |
| Zinc Oxide | 60 | 900–1100 |
| Cobalt Carbonate | 60 | 900–1100 |
| Cerium (III) carbonate | 60 | 900–1100 |

Restructuring is an observable phenomenon. Thus, it is also possible to experimentally determine desired times and temperatures. This can be done by sampling and analyzing a portion of the treated iron oxide, for example, by the B.E.T. surface area measurement method. The restructuring is then considered complete when the surface area is less than about 1.9 m²/g and the particle lengths lie between about 0.3 and about 3 µm and particle breadths lie between about 0.2 and about 2 µm.

After the iron oxide starting materials are heated they can be relaxed/cooled and yet retain their restructured physical characteristics. The simplest and preferred form of relaxation is to allow the iron oxide which has been heated to its restructuring point to cool undisturbed to about room temperature (20° C.). This generally takes between about ½ and 12 hours. The restructured material will retain its character over a broad range of conditions. Other forms of relaxation include any means to reduce the energy level of the restructured composition to include cooling to other temperatures at accelerated or decelerated rates. Preferred restructured compositions display structural stability over a range of temperatures which includes the range between about 500° and about 700° C. which is the temperature range wherein the catalytic conversion of ethylbenzene to styrene is preferably performed.

Restructured iron oxide may then be compounded, reacted, or prepared as a constituent of iron oxide catalysts in the manner well established in the art. That is, the restructured composition can be modified with V and/or Co as set forth in U.S. Pat. No. 4,098,723 or with Mo, Ca, and/or Cr as noted in U.S. Pat. No. 4,467,046, or with Al, Cd, Mg, Mn, Ni, U, and/or rare earths as noted in U.S. Pat. No. 4,152,300 each of which is incorporated herein by reference. Numerous other modifiers and promoters (such as K) known to those skilled in the art may be used. Modification of the composition is preferably done as an additional step after restructuring. That is, the restructured iron oxide is relaxed/cooled and then modified as per the iron oxide in the aforementioned patents.

Some physical aspects of the restructured iron oxide compositions may be observed by electron microscopy.

Figure 1:
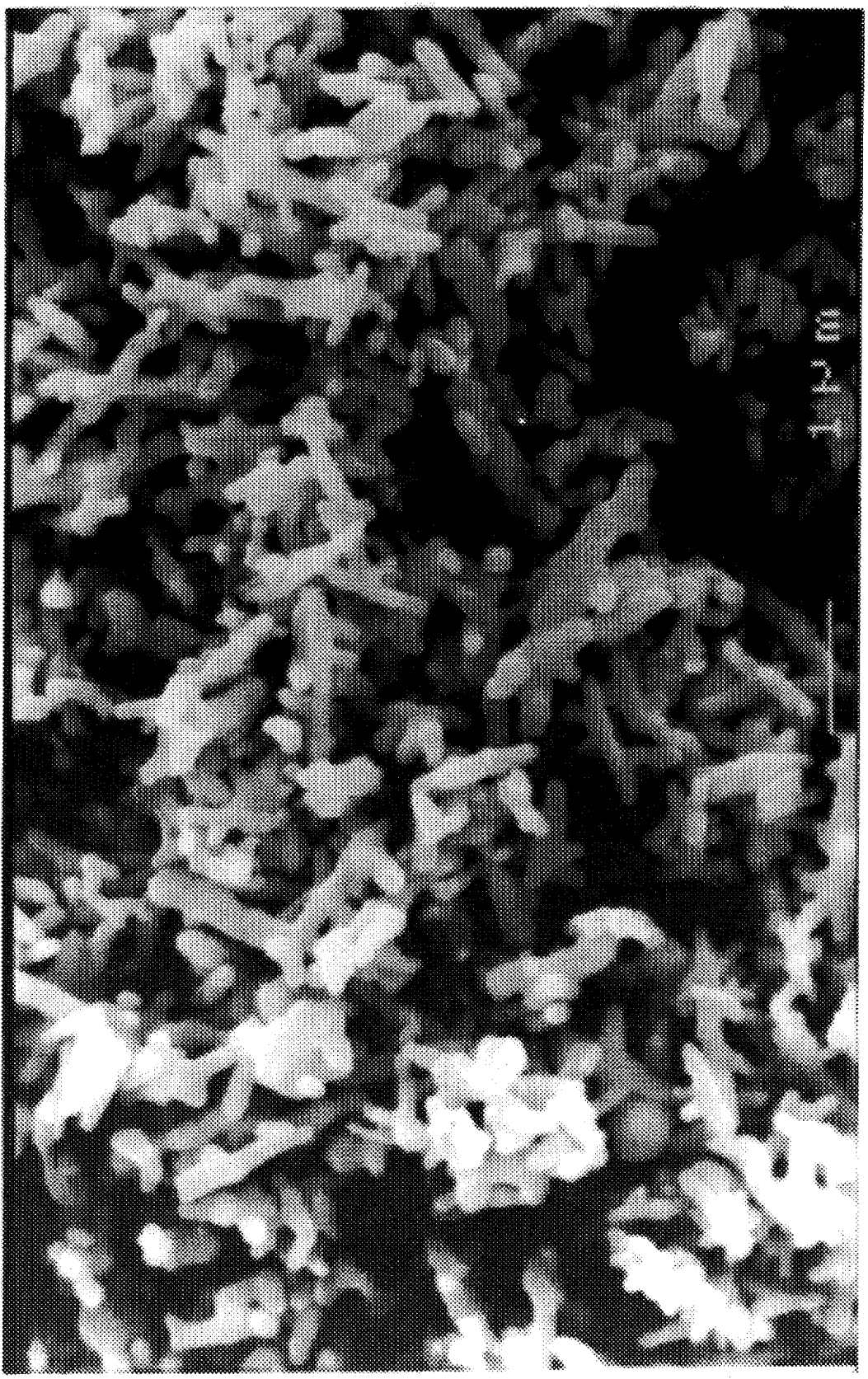
FIG. 1 is a scanning electron micrograph (10,000×) of branched acicular iron oxide which comprises one starting material of this invention.

FIG. 1 is an electron micrograph of a hematite starting material. The branched acicular structure of the particles can be plainly seen.

FIG. 2 shows the restructured hematite particles of this invention after restructuring with copper oxide. The more equant nature of the restructured particles is apparent as is the distinction between particles which share an interfacial joint.

Figure 3:
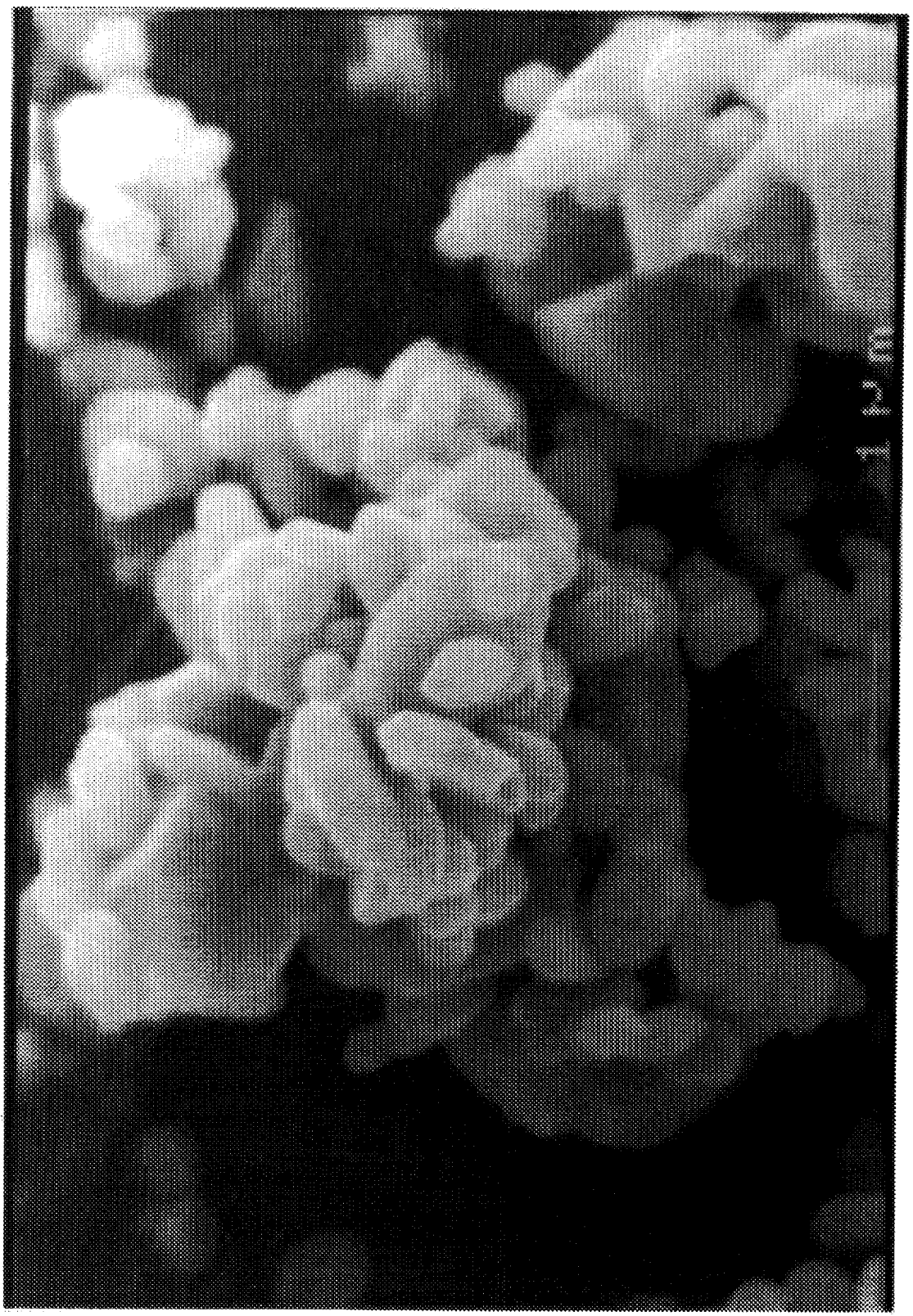
FIG. 3 is a scanning electron micrograph (10,000×) of iron oxide particles of this invention formed by restructuring red branched acicular iron oxide with ammonium dimolybdate.

FIG. 3 is an electron micrograph showing the restructured character of the particles wherein branched acicular red iron oxide was used as the starting material and ammonium dimolybdate was the restructuring agent.

Figure 4:
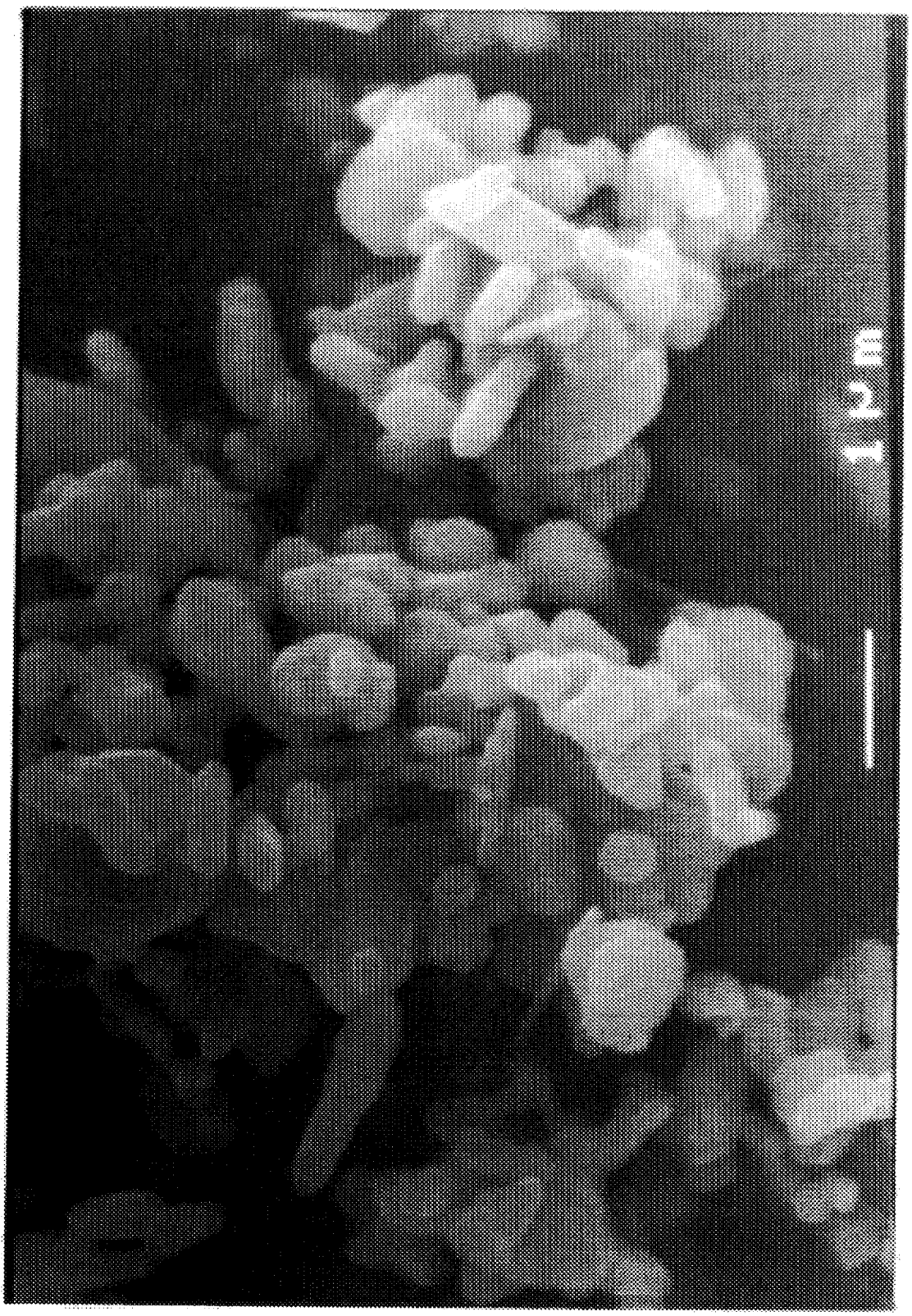
FIG. 4 is a scanning electron micrograph (10,000×) of iron oxide particles of this invention formed by restructuring yellow branched acicular iron oxide with molybdenum trioxide.

FIG. 4 is an electron micrograph showing the restructured character of the particles wherein branched acicular yellow iron oxide was used as the starting material and molybdenum trioxide was the restructuring agent.

Figure 5:
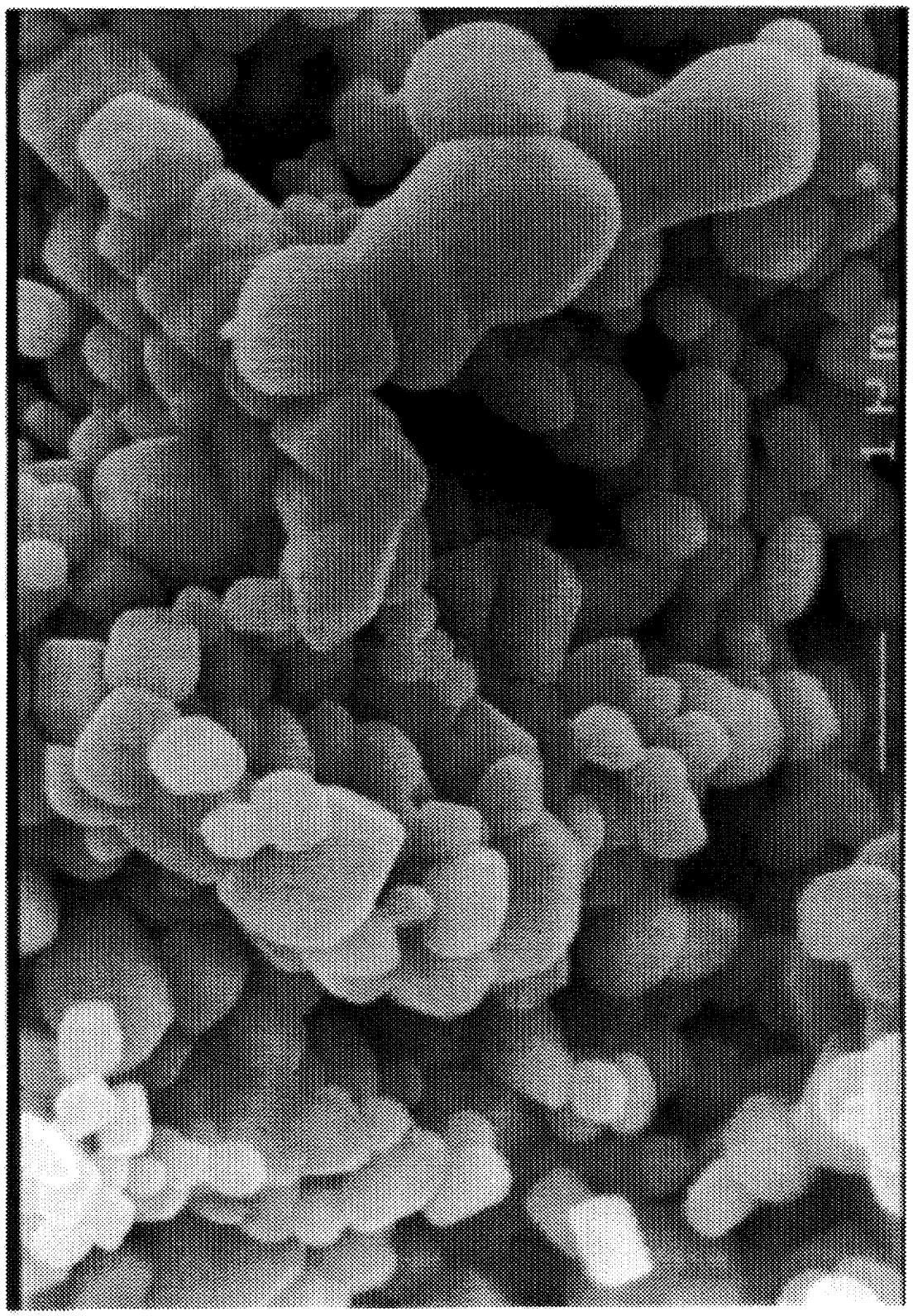
FIG. 5. is a scanning electron micrograph (10,000×) of the iron oxide particles of this invention formed by restructuring red random spheroidal iron oxide with molybdenum trioxide.

FIG. 5 is an electron micrograph showing restructured particles wherein random spheroidal red iron oxide was used as the starting material and molybdenum trioxide was the restructuring agent.

Figure 6:
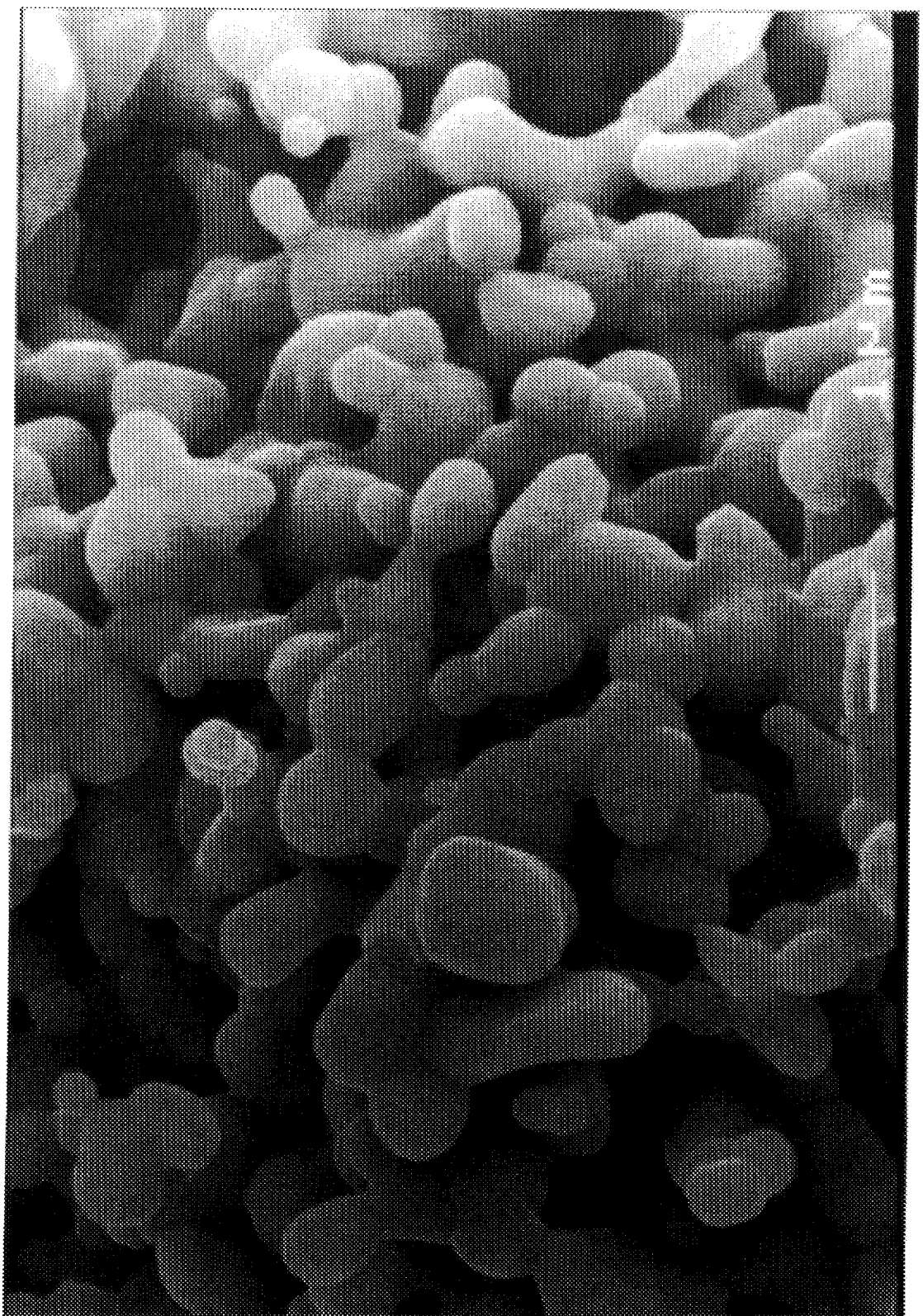
FIG. 6. is a scanning electron micrograph (10,000×) of the iron oxide particles of this invention formed by restructuring red branched acicular iron oxide with copper oxide.

FIG. 6 is an electron micrograph showing the restructured character of the particles wherein branched acicular red iron oxide was used as the starting material and copper oxide was the restructuring agent.

Restructured iron oxide can be formed into catalyst and used in dehydrogenation processes as described in copending application 08/355,949, now abandoned, filed on this same day entitled "Dehydrogenation Catalyst and Process" invented by Stanley Milam and Brent Shanks. Catalyst formation and use in dehydrogenation processes can also be conducted as set forth in U.S. Pat. No. 5,171,914 which is incorporated herein by reference. Generally, restructured iron oxide is mixed in a muller/mixer together with a mixture of oxides/hydroxides/carbonates of iron, potassium and one or more optional promoter metals. A small amount of water is added and the resulting paste is then extruded through a die to form, for example, pellets. The pellets are then dried at about 100° C. to about 300° C. and calcined at temperatures above 500° C., preferably between about 700° C. and about 1000° C. The restructured iron oxide that is used in the preparation of such a catalyst comprises between about 50 and 100% by weight of catalyst (basis iron oxide). Fillers and other common catalyst additives can also be present in such catalysts.

The invention is further illustrated by the following nonlimiting examples.

EXAMPLES

In each example that is not a comparative example, an iron oxide composition was first prepared by mixing iron oxide with various dry components (for about 10 minutes in a mixer-muller except as otherwise noted), adding de-ionized water or dilute aqueous $H_2SO_4$ and continuing mixing (for 5–15 minutes for a total mixing time of 25 minutes except as otherwise noted). The mixed components were then screened through a standard No. 7 sieve to break up any lumps, placed in dishes, and loaded into a muffle furnace at 170° C. These mixtures were then heated to the temperature indicated in the examples by ramping the furnace temperature at 6° C. per minute. The temperatures were maintained at the set point for one hour. Thereafter, the furnace was turned off and the iron oxide powder, treated as above, was allowed to cool to room temperature, in the furnace, over night (except as otherwise noted).

The iron oxide used in the comparative examples are the base cases for the examples according to the invention. That is, the iron oxide of the comparative examples is not restructured. Restructured iron oxide in the examples according to this invention is prepared by combination of the iron oxide of the comparative examples with a restructuring agent followed by treatment at the conditions specified in each given example. Thus, Comparative Example A is the base case (non-restructured) for Examples 1–15; Comparative Example B is the base case (non-restructured) for Examples 16–17; Comparative Example C is the base case (non-restructured) for Example 18; Comparative Example D is the base case (non-restructured) for Example 19; Comparative Example E is the base case (non-restructured) for Examples 20 and 21; Comparative Example F is the base case (non-restructured) for Example 22. Comparative Example G is the base case (non-restructured) for Example 23. Comparative examples H and I are comparative examples (non-restructured) without corresponding examples according to this invention.

Samples for electron microscopy/imagery analysis were prepared by sprinkling a small amount of iron oxide on a aluminum stub. The aluminum stub had a piece of conducting carbon tape on the top surface to hold the iron oxide in place. The stub/sample was then sputter coated with a thin layer (approximately 100 Å) of gold/palladium to enhance its conductivity.

The sample was placed in a scanning electron microscope (JEOL 6300FV SEM) and imaged at 50,000×; 25,000×; 10,000× and 5,000× magnifications. Permanent images were collected using Polaroid type 53 film as the recording media. Two areas, selected randomly, were photographed.

Apple Macintosh computers (PowerMacintosh 8100/80 AV, Quadra 700 and Macintosh II FX models) and LaCie Silverscan flatbed scanners were employed for image analyses along with PRISM v. 3.5 (a suite of programs from Analytical Vision of Raleigh, N.C., distributed by Signal Analytics of Vienna, Va., which includes PRISMView, PRISMScript, PRISMCalc and PRISMExec), Photoshop v. 3.0 (from Adobe), Excel v. 4.0 and Word v. 5.1 (from Microsoft), KaleidaGraph v. 2.1.3 (from AbelBeck Software), TRANSFORM v. 3.01 (from Spyglass of Champaign, Ill.) and IMAGE v. 1.52 (from the National Institutes of Health) software.

All images of agglomerated particles acquired at 10,000× magnification (including scale bars) were digitized at 256 gray levels and 150 dpi, ensuring that a consistent scanner white light brightness value is used for all image acquisitions and that no gamma correction is used. The image size was then altered to 72 dpi while keeping the file size and proportions constrained to allow the processing of all the pixels actually acquired. The 10,000× digitized images were analyzed by an experienced microscopist to identify particles within the agglomerate. Particles representative of the sample in terms of both size and shape were then manually outlined as the image was viewed with a computer at a (software) magnification high enough to discern individual pixels.

Proper segmentation and filling of the outlines described above then yielded binary images of each particles projection. After adjusting the scale of the images to correspond to the scale marker digitized with the image, each of the particles contained within that digitized image was measured using the PRISMView program to determine parameters such as length, breadth, and aspect ratio. (See Russ, J. C. *Computer Assisted Microscopy*, Plenum Press, NY, N.Y. (1991).

Surface area measurements for the non-restructured iron oxide starting materials and the restructured iron oxide products were measured using the triple point B.E.T. method. Krypton gas was used for materials whose surface area was less than 10 $m^2$/gram as per ASTM method D4780-88. Nitrogen gas was used for materials whose surface area was greater than 10 $m^2$/gram as per ASTM method D3663-92 except that three data points were collected and processed rather than four as specified in the ASTM method. All samples, except Example G, were degassed in vacuum at 300° to 400° C. for about 4 hours prior to the surface area measurement. The non-restructured branched acicular synthetic yellow iron oxide, Example G, was degassed in vacuum at 150° C. for about 2 hours prior to the surface area measurement. The lower degassing temperature for Example G was necessary to avoid conversion of the material to red iron oxide.

The average of the numerical values obtained from imagery analysis and surface area determination for non-restructured iron oxides and restructured iron oxides of the examples are summarized in Table 2 below.

To test the catalytic effect of restructuring the iron oxide, each mixture formed as outlined above and each iron oxide comparative example sample was then formed into ⅛ inch catalyst pellets. This was done by taking the iron oxide composition and mixing it with various ingredients for about 10 minutes in a mixer-muller except as otherwise noted, adding de-ionized water and continuing mixing (for 5–15 minutes for a total mixing time of 25 minutes except as otherwise noted). The mixed components were then screened through a standard No. 7 sieve to break up any lumps and then processed through a laboratory scale California Pellet Mill. The pellets so obtained were then dried for about 15–60 minutes at 170° C. in an electrically heated drying oven and then transferred to an electrically heated muffle furnace where they were calcined at 800°–825° C. for about one hour.

The catalyst pellets were then used in the preparation of styrene from ethylbenzene under isothermal conditions in a reactor designed for continuous operation. The conditions of the catalyst test were as follows: 100 $cm^3$ of catalyst, 600° C. reactor temperature, LHSV of 0.65 measured in liters of ethylbenzene per liter of catalyst per hour, a steam to ethylbenzene molar ratio of 10:1, and a reactor pressure of 0.75 atmospheres.

The catalyst testing results are reported in terms of $T_{70}$ and $S_{70}$ where $T_{70}$ is the temperature required for a given catalyst to convert 70% of the ethylbenzene feed to products and $S_{70}$ is the molar selectivity to product styrene.

Catalytic performance data for catalysts made from non-restructured iron oxide and the restructured iron oxide of the examples are summarized in Table 3 below.

Example A (Comparative)

Non-Restructured Synthetic Red Iron Oxide.

An iron oxide catalyst was prepared by adding 18.6 grams of calcium carbonate, 126.0 grams of cerium (III) carbonate, 25.8 grams of ammonium dimolybdate, and 255.1 grams of potassium carbonate, to 1103.5 grams of non-restructured branched acicular synthetic red iron oxide; 201.3 grams of de-ionized water was added in the mixing step.

Example 1-A

Red Iron Oxide Treated with Ammonium Dimolybdate:

An iron oxide composition was formed by adding 1204 grams of branched acicular synthetic red iron oxide to 28.1 grams of ammonium dimolybdate in the process noted above; 220 grams of de-ionized water was added during the mixing step and the mixture was ultimately heated to 750° C.

The resulting iron oxide composition had altered physical characteristics but did not completely restructure due to low treatment temperature and/or treatment time.

Catalyst ingredients included 18.6 grams of calcium carbonate, 126.0 grams of cerium (III) carbonate, 255.1 grams of potassium carbonate, and 1121.8 grams of treated iron oxide; 106.8 grams of de-ionized water was added during the mixing step of catalyst preparation.

Example 1-B

Red Iron Oxide Restructured with Ammonium Dimolybdate:

A restructured iron oxide composition was formed by adding 1204 grams of branched acicular synthetic red iron oxide to 28.1 grams of ammonium dimolybdate in the process noted above; 220 grams of de-ionized water was added to the mixture during the mixing step and the mixture was ultimately heated to 825° C.

Catalyst ingredients included 18.6 grams of calcium carbonate, 126.0 grams of cerium (III) carbonate, 255.1 grams of potassium carbonate, and 1121.8 grams of restructured iron oxide; 82.2 grams of de-ionized water was added during the mixing step of catalyst preparation.

Example 1-C

Red Iron Oxide Restructured with Ammonium Dimolybdate:

A restructured iron oxide composition was formed by mixing 1204 grams of branched acicular synthetic red iron oxide with 28.1 grams of ammonium dimolybdate in the process noted above; 220 grams of de-ionized water was added to the mixture during the mixing step and the mixture was ultimately heated to 900° C.

Catalyst ingredients included 19.0 grams of calcium carbonate, 128.5 grams of cerium (III) carbonate, 260.2 grams of potassium carbonate, and 1143.6 grams of restructured iron oxide; 63.7 grams of de-ionized water was added during the mixing step of catalyst preparation.

Example 1-D

Red Iron Oxide Restructured with Ammonium Dimolybdate:

A restructured iron oxide composition was formed by mixing 1500 grams of branched acicular synthetic red iron oxide and 35.1 grams of ammonium dimolybdate in the process noted above; 250 grams of de-ionized water was added during the mixing step and the mixture was ultimately heated to 950° C.

Catalyst ingredients included 18.6 grams of calcium carbonate, 126.0 grams of cerium (III) carbonate, 255.1 grams of potassium carbonate, and 1121.8 grams of restructured iron oxide; 54.8 grams of de-ionized water was added to the mixture during the mixing step of catalyst preparation.

Example 2-A

Red Iron Oxide Restructured with Copper (II) Oxide:

A restructured iron oxide composition was formed by mixing 1208.0 grams of branched acicular synthetic red iron oxide and 9.7 grams of copper oxide in the process noted above; 110 grams of de-ionized water was added to the mixture during the mixing step and the mixture was heated to 975° C. by inserting it into the furnace preheated to 975° C. The restructured iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1108.9 grams of restructured iron oxide; 89.6 grams of de-ionized water was added to the mixture during the mixing step of catalyst preparation.

Example 2-B

Red Iron Oxide Restructured with Copper (II) Oxide:

A restructured iron oxide composition was formed by mixing 1208.0 grams of branched acicular synthetic red iron oxide and 19.4 grams of copper oxide in the process noted above; 110 grams of de-ionized water was added to the mixture during the mixing step and the mixture was heated to 975° C. by inserting it into the furnace preheated to 975° C. The restructured iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1117.8 grams of restructured iron oxide; 100.1 grams of de-ionized water was added to the mixture during the mixing step of catalyst preparation.

Example 2-C

Red Iron Oxide Restructured with Copper (II) Oxide:

A restructured iron oxide composition was prepared by mixing 1208.0 grams of branched acicular synthetic red iron oxide and 29.1 grams of copper oxide in the process noted above; 110 grams of de-ionized water was added to the mixture during the mixing step and the mixture was heated to 975° C. by inserting it into the furnace preheated to 975° C. The restructured iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1126.6 grams of restructured iron oxide; 87.2 grams of de-ionized water was added to the mixture during the mixing step of catalyst preparation.

Example 2-D

Red Iron Oxide Restructured with Copper (II) Oxide:

A restructured iron oxide composition was prepared by mixing 1208.0 grams of branched acicular synthetic red iron oxide and 48.4 grams of copper oxide in the process noted above; 110 grams of de-ionized water was added to the mixture during the mixing step and the mixture was heated to 975° C. by inserting it into the furnace preheated to 975° C. The restructured iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1144.4 grams of restructured iron oxide; 113.5 grams of de-ionized water was added to the mixture during the mixing step of catalyst preparation.

Example 3

Red Iron Oxide Restructured with Calcium (II) Acetate:

A restructured iron oxide composition was prepared by mixing 1200.0 grams of branched acicular synthetic red iron oxide and 32.0 grams of calcium acetate dissolved in 150 grams of de-ionized water, over 15 minutes, while mulling (mixing). The mixture was placed in stainless steel dishes, dried in an electrically heated drying oven, 30 minutes at 170° C., and then was and loaded into an electrically heated muffle furnace at 700° C. Air flow through the furnace was maintained at 40 scf/hr throughout the calcination. The furnace temperature was ramped to 900° C., over one hour, and was maintained at that set point temperature for one hour. Thereafter, the furnace was turned off and the iron oxide powder, treated as above, was allowed to cool to room temperature, over night.

Catalyst ingredients included 121.3 grams of cerium (III) carbonate, 25.6 grams of ammonium dimolybdate, 245.6 grams of potassium carbonate, and 1110.4 grams of restructured iron oxide; 92.3 grams of de-ionized water was added to the mixture during the mixing step of catalyst preparation.

Example 4

Red Iron Oxide Restructured with Zinc (II) Oxide:

Restructured iron oxide was prepared by mixing 1200.0 grams of branched acicular synthetic red iron oxide and 19.9 grams of zinc oxide in the process noted above; 220 grams of de-ionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1118.2 grams of restructured iron oxide; 125.0 grams of de-ionized water was added to the mixture during the mixing step of catalyst preparation.

Example 5

Red Iron Oxide Treated with Tin (IV) Oxide:

An iron oxide composition was prepared by mixing 1200.0 grams of branched acicular synthetic red iron oxide and 36.7 grams of tin oxide in the process noted above; 220 grams of de-ionized water was added to the mixture during the mixing step and the mixture was ultimately heated to 975° C.

The resulting iron oxide composition had altered physical characteristics but did not completely restructure due to low treatment temperature and/or treatment time. Heating for an additional hour at this temperature or increasing the initial temperature to about 1050° C. for the same period of time will result in restructuring.

Catalyst ingredients included 18.6 grams of calcium carbonate, 126.0 grams of cerium (III) carbonate, 25.8 grams of ammonium dimolybdate, 255.1 grams of potassium carbonate, and 1133.6 grams of treated iron oxide; 146.5 grams of de-ionized water was added to the mixture during the mixing step of catalyst preparation.

Example 6

Red Iron Oxide Restructured with Manganese (IV) Oxide:

A restructured iron oxide composition was prepared by mixing 1200.0 grams of branched acicular synthetic red iron oxide and 21.2 grams of manganese oxide in the process noted above; 220 grams of de-ionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1119.4 grams of restructured iron oxide; 116.8 grams of de-ionized water was added to the mixture during the mixing step of catalyst preparation.

Example 7

Red Iron Oxide Treated with Vanadium (V) Oxide:

An iron oxide composition was prepared by mixing 1203.0 grams of branched acicular synthetic red iron oxide and 22.1 grams of vanadium oxide in the process noted above; 220 grams of de-ionized water was added to the mixture during the mixing step and the mixture was ultimately heated to a temperature of 700° C.

The resulting iron oxide composition had altered physical characteristics but did not completely restructure due to low treatment temperature and/or treatment time.

Catalyst ingredients included 18.6 grams of calcium carbonate, 126.0 grams of cerium (lit) carbonate, 25.8 grams of ammonium dimolybdate, 255.1 grams of potassium carbonate, and 1120.3 grams of treated iron oxide; 154.0 grams of de-ionized water was added to the mixture during the mixing step of catalyst preparation.

Example 8

Red Iron Oxide Restructured with Titanium (IV) Oxide:

A restructured iron oxide composition was prepared by mixing 1200.0 grams of branched acicular synthetic red iron oxide and 19.4 grams of titanium oxide in the process noted above; 220 grams of de-ionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1117.8 grams of restructured iron oxide; 115.0 grams of de-ionized water was added to the mixture during the mixing step of catalyst preparation.

Example 9

Red Iron Oxide Treated with Niobium (V) Oxide:

An iron oxide composition was prepared by mixing 1200.0 grams of branched acicular synthetic red iron oxide and 32.4 grams of niobium oxide in the process noted above; 220 grams of de-ionized water was added to the mixture during the mixing step and the mixture was ultimately heated to 975° C.

The resulting iron oxide composition had altered physical characteristics but did not completely restructure due to low treatment temperature and/or treatment time.

Catalyst ingredients included 18.6 grams of calcium carbonate, 126.0 grams of cerium (III) carbonate, 25.8 grams of ammonium dimolybdate, 255.1 grams of potassium carbonate, and 1129.7 grams of treated iron oxide;

146.2 grams of de-ionized water was added to the mixture during the mixing step of catalyst preparation.

Example 10

Red Iron Oxide Treated with Antimony (III) Oxide:

An iron oxide composition was prepared by mixing 1200.0 grams of branched acicular synthetic red iron oxide and 39.4 grams of antimony oxide in the process noted above; 220 grams of de-ionized water was added to the mixture during the mixing step and the mixture was ultimately heated to 700° C.

The resulting iron oxide composition had altered physical characteristics but did not completely restructure due to low treatment temperature and/or treatment time. Increasing the initial temperature to about 900° C. for the same period of time will result in restructuring.

Catalyst ingredients included 18.6 grams of calcium carbonate, 126.0 grams of cerium (III) carbonate, 25.8 grams of ammonium dimolybdate, 255.1 grams of potassium carbonate, and 1136.1 grams of treated iron oxide; 148.4 grams of de-ionized water was added to the mixture during the mixing step of catalyst preparation.

Example 11

Red Iron Oxide Treated with Bismuth (III) Oxide:

An iron oxide composition was prepared by mixing 1200.0 grams of branched acicular synthetic red iron oxide and 56.7 grams of bismuth oxide in the process noted above; 220 grams of de-ionized water was added to the mixture during the mixing step and the mixture was ultimately heated to 825° C.

The resulting iron oxide composition had altered physical characteristics but did not completely restructure due to low treatment temperature and/or treatment time. Heating for an additional hour at this temperature or increasing the initial temperature to about 900° C. for the same period of time will result in restructuring.

Catalyst ingredients included 18.6 grams of calcium carbonate, 126.0 grams of cerium (III) carbonate, 25.8 grams of ammonium dimolybdate, 255.1 grams of potassium carbonate, and 1152.0 grams of treated iron oxide; 136.3 grams of de-ionized water was added to the mixture during the mixing step of catalyst preparation.

Example 12

Red Iron Oxide Treated with Yttrium (III) Carbonate Hydrate:

An iron oxide composition was prepared by mixing 1204.0 grams of branched acicular synthetic red iron oxide and 43.6 grams of yttrium carbonate in the process noted above; 220 grams of de-ionized water was added to the mixture during the mixing step and the mixture was ultimately heated to 975° C.

The resulting iron oxide composition had altered physical characteristics but did not completely restructure due to low treatment temperature and/or treatment time. Heating for an additional hour at this temperature or increasing the initial temperature to about 1050° C. for the same period of time will result in restructuring.

Catalyst ingredients included 18.6 grams of calcium carbonate, 126.9 grams of cerium (III) carbonate, 25.8 grams of ammonium dimolybdate, 255.3 grams of potassium carbonate, and 1125.2 grams of treated iron oxide; 174.3 grams of de-ionized water was added to the mixture during the mixing step of catalyst preparation.

Example 13

Red Iron Oxide Restructured with Cobalt (II) Carbonate:

A restructured iron oxide composition was prepared by mixing 1204.0 grams of branched acicular synthetic red iron oxide and 29.0 grams of cobalt carbonate in the process noted above; 220 grams of de-ionized water was added to the mixture during the mixing step and the mixture was ultimately heated to 975° C.

Catalyst ingredients included 18.6 grams of calcium carbonate, 126.9 grams of cerium (III) carbonate, 25.8 grams of ammonium dimolybdate, 255.3 grams of potassium carbonate, and 1116.7 grams of restructured iron oxide; 125.0 grams of de-ionized water was added to the mixture during the mixing step of catalyst preparation.

Example 14

Red Iron Oxide Restructured with Cerium (III) Carbonate:

A restructured iron oxide composition was prepared by mixing 1204.0 grams of branched acicular synthetic red iron oxide and 68.0 grams of cerium (III) carbonate in the process noted above; 220 grams of de-ionized water was added to the mixture during the mixing step and the mixture was ultimately heated to 975° C.

Catalyst ingredients included 18.6 grams of calcium carbonate, 126.9 grams of cerium (Ill) carbonate, 25.8 grams of ammonium dimolybdate, 255.3 grams of potassium carbonate, and 1138.4 grams of restructured iron oxide; 142.0 grams of de-ionized water was added to the mixture during the mixing step of catalyst preparation.

Example 15

Red Iron Oxide Treated with Lanthanum (III) Hydroxide:

An iron oxide composition was prepared by mixing 1204.0 grams of branched acicular synthetic red iron oxide and 46.2 grams of lanthanum hydroxide in the process noted above; 220 grams of de-ionized water was added to the mixture during the mixing step and the mixture was ultimately heated to 975° C.

The resulting iron oxide composition had altered physical characteristics but did not completely restructure due to low treatment temperature and/or treatment time. Heating for an additional hour at this temperature or increasing the initial temperature to about 1050° C. for the same period of time will result in restructuring.

Catalyst ingredients included 18.6 grams of calcium carbonate, 126.9 grams of cerium (III) carbonate, 25.8 grams of ammonium dimolybdate, 255.3 grams of potassium carbonate, and 1136.4 grams of treated iron oxide; 172.2 grams of de-ionized water was added to the mixture during the mixing step of catalyst preparation.

Example B (Comparative)

Catalyst Prepared with Non-Restructured Synthetic Red Iron Oxide:

An iron oxide catalyst was prepared by adding 20.1 grams of calcium carbonate, 103.1 grams of cerium (III) carbonate, 32.3 grams of ammonium paratungstate, and 200.9 grams of potassium carbonate, to 902.9 grams of non-restructured branched acicular synthetic red iron oxide; 119.1 grams of de-ionized water was added to the mixture during the mixing step.

Example 16

Red Iron Oxide Restructured with Ammonium Paratungstate:

A restructured iron oxide composition was prepared by mixing 1500 grams of branched acicular synthetic red iron oxide and 53.8 grams of ammonium paratungstate in the process noted above; 250 grams of de-ionized water was added to the mixture during the mixing step and the mixture was ultimately heated to 950° C.

Catalyst ingredients included 24.8 grams of calcium carbonate, 126.0 grams of cerium (III) carbonate, 255.6 grams of potassium carbonate, and 1135.2 grams of restructured iron oxide; 81.4 grams of de-ionized water was added to the mixture during the mixing step of catalyst preparation.

Example 17

Red Iron Oxide Restructured with Tungsten (VI) Oxide:

A restructured iron oxide composition was prepared by mixing 1500 grams of branched acicular synthetic red iron oxide and 47.9 grams of tungsten oxide in the process noted above; 250 grams of de-ionized water was added to the mixture during the mixing step and the mixture was ultimately heated to 950° C.

Catalyst ingredients included 24.8 grams of calcium carbonate, 126.0 grams of cerium (III) carbonate, 255.6 grams of potassium carbonate, and 1135.2 grams of restructured iron oxide; 81.4 grams of de-ionized water was added to the mixture during the mixing step of catalyst preparation.

Example C (Comparative)

Catalyst Prepared with Non-Restructured Synthetic Red Iron Oxide:

A catalyst was prepared by adding 10.5 grams of calcium carbonate, 119.5 grams of cerium (III) carbonate, 39.2 grams of ammonium paratungstate, 8.8 grams of chromium oxide, 17.1 grams of magnesium carbonate, and 259.9 grams of potassium carbonate, to 1105.5 grams of non-restructured branched acicular synthetic red iron oxide; 162.5 grams of de-ionized water was added to the mixture during the mixing step.

Example 18

Red Iron Oxide Restructured with Chromium (III) Nitrate:

A restructured iron oxide composition was prepared by mixing 1200 grams of branched acicular synthetic red iron oxide and 24.2 grams of chromium nitrate dissolved in 150 grams of de-ionized water, over 15 minutes, while mulling (mixing). The mixture was placed in ceramic dishes, dried in an electrically heated drying oven, 30 minutes at 170° C., and then was loaded into an electrically heated muffle furnace at 700° C. Air flow through the furnace was maintained at 40 scf/hr throughout the calcination. The furnace temperature was ramped to 950° C., over one hour, and was maintained at that set point temperature for one hour. Thereafter, the furnace was turned off and the iron oxide powder, treated as above, was allowed to cool to room temperature, in the furnace, over night.

Catalyst ingredients included 9.9 grams of calcium carbonate, 120.9 grams of cerium (III) carbonate, 39.2 grams of ammonium paratungstate, 17.1 grams of magnesium carbonate, 245.4 grams of potassium carbonate, and 1108.5 grams of restructured iron oxide; 119.4 grams of de-ionized water was added to the mixture during the mixing step of catalyst preparation.

Example D (Comparative)

Catalyst Prepared with Non-Restructured Synthetic Red Iron Oxide:

A catalyst was prepared by adding 18.5 grams of calcium carbonate, 119.8 grams of cerium (III) carbonate, 25.6 grams of ammonium dimolybdate, and 245.6 grams of potassium carbonate, to 1103.2 grams of non-restructured random spheroidal synthetic red iron oxide; 157.2 grams of de-ionized water was added to the mixture during the mixing step.

Example 19

Red Iron Oxide Restructured with Molybdenum (VI) Oxide:

A restructured iron oxide composition was prepared by mixing 1200 grams of random spheroidal synthetic red iron oxide and 47.7 grams of molybdenum trioxide according the process noted above; 220 grams of de-ionized water was added to the mixture during the mixing step and the mixture was ultimately heated to 825° C.

Catalyst ingredients included 17.7 grams of calcium carbonate, 115.7 grams of cerium (III) carbonate, 242.5 grams of potassium carbonate, and 1086.4 grams of restructured iron oxide; 94.8 grams of de-ionized water was added to the mixture during the mixing step of catalyst preparation.

Example E (Comparative)

Catalyst Prepared with Non-Restructured Synthetic Red Iron Oxide:

A catalyst was prepared by adding 20.3 grams of calcium carbonate, 103.1 grams of cerium (III) carbonate, 32.3 grams of ammonium paratungstate, and 200.9 grams of potassium carbonate, to 900.0 grams of non-restructured random spheroidal synthetic red iron oxide; 124.6 grams of de-ionized water was added to the mixture during the mixing step.

Example 20

Red Iron Oxide Restructured with Magnesium Nitrate:

A restructured iron oxide composition was prepared by mixing 1200 grams of random spheroidal synthetic red iron oxide and 69.4 grams of magnesium nitrate dissolved in 100 grams of de-ionized water, over 15 minutes, while mulling (mixing). The mixture was placed in ceramic dishes and then was loaded into an electrically heated muffle furnace at 170° C. and dried for 30 minutes. The furnace temperature was then ramped, at 6° C./min. from 170 to 950° C., and was maintained at 950° C. for one hour. Air flow through the furnace was maintained at 40 scf/hr throughout the calcination. Thereafter, the furnace was turned off and the iron oxide powder, treated as above, was allowed to cool to room temperature, in the furnace, over night.

Catalyst ingredients included 20.3 grams of calcium carbonate, 102.8 grams of cerium (III) carbonate, 32.1 grams of ammonium paratungstate, 200.8 grams of potassium carbonate, and 908.2 grams of restructured iron oxide; 80.2 grams of de-ionized water was added to the mixture during the mixing step of catalyst preparation.

Example 21

Red Iron Oxide Restructured with Potassium Permanganate:

A restructured iron oxide composition was prepared by mixing 1200 grams of random spheroidal synthetic red iron oxide and 10.0 grams of potassium permanganate dissolved in 250 grams of de-ionized water, over 15 minutes, while mulling (mixing). The mixture was screened through a standard No. 7 sieve to break up any lumps and then was placed in ceramic dishes and loaded into an electrically heated muffle furnace at 170° C. The furnace temperature was then ramped at 6° C./min. to 950° C. and was maintained at the set point temperature for one hour. Thereafter, the furnace was turned off and the iron oxide powder, treated as above, was allowed to cool to room temperature, in the furnace, over night.

Catalyst ingredients included 22.5 grams of calcium carbonate, 114.5 grams of cerium (III) carbonate, 35.8 grams of ammonium paratungstate, 232.4 grams of potassium carbonate, and 1000.0 grams of restructured iron oxide; 118.0 grams of de-ionized water was added to the mixture during the mixing step of catalyst preparation.

Example F (Comparative)

Catalyst Prepared with Non-Restructured Synthetic Red Iron Oxide:

A catalyst was prepared by adding 60.0 grams of cerium (III) carbonate, 29.8 grams of ammonium paratungstate, 14.0 grams of chromium oxide, 21.0 grams of vanadium oxide, and 287.5 grams of potassium carbonate, to 1105.5 grams of non-restructured random spheroidal synthetic red iron oxide; 156.7 grams of de-ionized water was added to the mixture during the mixing step.

Example 22

Red Iron Oxide Restructured with Vanadium (V) Oxide:

A restructured iron oxide composition was prepared by mixing 1200 grams of random spheroidal synthetic red iron oxide and 24.2 grams of vanadium oxide in the process noted above. The dry solids were mulled (mixed) for 10 minutes; thereafter, 150 cm$^3$ of a dilute sulfuric acid solution (10.0 grams of concentrated $H_2SO_4$ diluted to 150 cm$^3$) was added to the mixture during the mixing step and the mixture was ultimately heated to 825° C.

Catalyst ingredients included 58.7 grams of cerium (III) carbonate, 26.7 grams of ammonium paratungstate, 12.5 grams of chromium oxide, 266.6 grams of potassium carbonate, and 1018.5 grams of restructured iron oxide; 74.7 grams of de-ionized water was added to the mixture during the mixing step of catalyst preparation.

Example G (Comparative)

Catalyst Prepared with Non-Restructured Synthetic Yellow Iron Oxide:

A catalyst was prepared by adding 18.6 grams of calcium carbonate, 126.0 grams of cerium (III) carbonate, 25.8 grams of ammonium dimolybdate, and 255.3 grams of potassium carbonate, to 1290.9 grams of non-restructured branched acicular synthetic yellow iron oxide; 214.2 grams of de-ionized water was added to the mixture during the mixing step.

Example 23

Yellow Iron Oxide Treated with Molybdenum (VI) Oxide:

An iron oxide composition was prepared by mixing 1408.3 grams of branched acicular synthetic yellow iron oxide and 47.6 grams of molybdenum oxide in the process noted above; 220 grams of de-ionized water was added to the mixture during the mixing step and the mixture was ultimately heated to 800° C.

The resulting iron oxide composition had altered physical characteristics but did not completely restructure due to low treatment temperature and/or treatment time.

Catalyst ingredients included 18.6 grams of calcium carbonate, 126.0 grams of cerium (III) carbonate, 255.3 grams of potassium carbonate, and 1143.6 grams of treated iron oxide; 91.7 grams of de-ionized water was added to the mixture during the mixing step of catalyst preparation.

Example H (Comparative)

Yellow Iron Oxide Treated with Chromium (III) Oxide:

A non-restructured branched acicular synthetic red iron oxide composition was prepared by mixing 704.15 grams of non-restructured branched acicular synthetic yellow iron oxide and 4.4 grams of chromium oxide in the process noted above; 110 grams of de-ionized water was added to the mixture during the mixing step and the mixture was ultimately heated to 500° C.

Example I (Comparative)

Heated Iron Oxide

An iron oxide composition was prepared by mixing 1200 grams of branched acicular synthetic red iron oxide and 220 grams of de-ionized water were mixed and the mixture was ultimately heated to 950° C.

This iron oxide composition did not restructure despite the significant heating. This was due to the absence of a restructuring agent.

TABLE 2

Characteristics of Restructured Iron Oxides and Base Case Non-Restructured Precursors Thereto

| Example | Average Particle length, microns | Average Particle Breadth, microns | Particle Aspect Ratio | Iron Oxide Surface Area, m$^2$/g |
|---|---|---|---|---|
| Comp. Ex. A | 0.9 | 0.4 | 2.2 | 4.0 |
| 1-A | 0.7 | 0.4 | 1.7 | 3.8 |
| 1-B | 1.0 | 0.7 | 1.4 | 1.4 |
| 1-C | 2.0 | 1.5 | 1.3 | 0.4 |
| 1-D | 2.5 | 1.9 | 1.3 | 0.2 |
| 2-A | 0.8 | 0.6 | 1.3 | 1.0 |
| 2-B | 0.8 | 0.6 | 1.3 | 1.0 |
| 2-C | 0.8 | 0.6 | 1.3 | 1.1 |
| 2-D | 0.9 | 0.6 | 1.5 | 1.0 |
| 3 | 1.1 | 0.7 | 1.6 | 1.6 |
| 4 | 0.7 | 0.5 | 1.4 | 1.6 |
| 5 | 0.6 | 0.4 | 1.5 | 1.9 |
| 6 | 0.7 | 0.5 | 1.4 | 1.5 |
| 7 | 0.6 | 0.3 | 2.0 | 3.9 |
| 8 | 0.8 | 0.5 | 1.6 | 1.4 |
| 9 | 0.7 | 0.4 | 1.7 | 1.8 |
| 10 | 0.6 | 0.3 | 2.0 | 4.3 |
| 11 | 0.4 | 0.3 | 1.3 | 2.4 |
| 12 | 0.7 | 0.4 | 1.7 | 2.3 |
| 13 | 0.8 | 0.5 | 1.6 | 1.3 |
| 14 | 0.7 | 0.5 | 1.4 | 1.7 |
| 15 | 0.7 | 0.4 | 1.7 | 2.3 |
| Comp. Ex. B | 0.9 | 0.4 | 2.2 | 4.0 |
| 16 | 0.7 | 0.4 | 1.7 | 1.0 |
| 17 | 0.7 | 0.5 | 1.4 | 1.2 |
| Comp. Ex. C | 0.9 | 0.4 | 2.2 | 4.0 |
| 18 | 0.5 | 0.4 | 1.2 | 1.6 |
| Comp. Ex. D | 0.4 | 0.3 | 1.3 | 3.8 |
| 19 | 0.9 | 0.6 | 1.5 | 1.2 |
| Comp. Ex. E | 0.4 | 0.3 | 1.3 | 3.8 |
| 20 | 0.6 | 0.4 | 1.5 | 1.4 |
| 21 | 0.7 | 0.5 | 1.4 | 1.6 |
| Comp. Ex. F | 0.4 | 0.3 | 1.3 | 3.8 |
| 22 | 1.9 | 1.5 | 1.3 | 0.4 |
| Comp. Ex. G | 0.5 | 0.2 | 2.5 | 17.4 |
| 23 | 0.7 | 0.4 | 1.7 | 1.9 |
| Comp. Ex. H | 0.5 | 0.2 | 2.5 | 63 |
| Comp. Ex. I | 0.9 | 0.5 | 1.8 | 1.9 |

The data in Table 2 shows the reduction in surface area concomitant with restructuring the iron oxide particles. Further, it can be seen that one or both of the dimensions of the particles (length or breadth) grows relative to the starting material. Examples 1A–1D show that increasing the temperature at a fixed amount of restructuring agent and fixed restructuring time results in larger particles as measured by particle length and breadth and that the surface area of the particles decreases as the particle size increases.

TABLE 3

Catalyst Physical Properties and Performance Results

| Example | Catalyst Median Pore Diameter, Angstroms | Catalyst Pore Volume, cm³/g | $T_{70}$ | $S_{70}$ |
|---|---|---|---|---|
| Comp. Ex. A | 2,743 | 0.1941 | 595 | 94.4 |
| 1-A | 2,281 | 0.1271 | 596 | 95.0 |
| 1-B | 6,654 | 0.0979 | 596 | 96.0 |
| 1-C | 9,524 | 0.0707 | 600 | 96.4 |
| 1-D | 14,816 | 0.1024 | 609 | 96.4 |
| 2-A | 6,255 | 0.1324 | 596 | 95.7 |
| 2-B | 5,459 | 0.145 | 598 | 95.3 |
| 2-C | 4,898 | 0.1348 | 595 | 95.0 |
| 2-D | 5,679 | 0.1421 | 594 | 94.0 |
| 3 | 3,830 | 0.112 | 590 | 96.0 |
| 4 | 4,871 | 0.1471 | 598 | 95.6 |
| 5 | 4,334 | 0.1482 | 602 | 95.1 |
| 6 | 4,403 | 0.1243 | 597 | 95.3 |
| 7 | 2,929 | 0.1587 | 611 | 95.3 |
| 8 | 4,915 | 0.1335 | 599 | 95.2 |
| 9 | 4,246 | 0.1445 | 640* | 91.5* |
| 10 | 2,048 | 0.1452 | 664* | 86.9* |
| 11 | 7,158 | 0.1256 | 602 | 95.7 |
| 12 | 4,205 | 0.1613 | 606 | 93.5 |
| 13 | 5,057 | 0.1408 | 598 | 95.6 |
| 14 | 4,698 | 0.1462 | 594 | 95.3 |
| 15 | 3,643 | 0.1548 | 596 | 94.0 |
| Comp. Ex. B | 2,519 | 0.1688 | 603 | 95.0 |
| 16 | 5,111 | 0.0895 | 606 | 95.9 |
| 17 | 4,229 | 0.0931 | 605 | 95.8 |
| Comp. Ex. C | 2,390 | 0.163 | 588 | 92.2 |
| 18 | 4,420 | 0.151 | 588 | 95.3 |
| Comp. Ex. D | 3,625 | 0.1679 | 594 | 95.7 |
| 19 | 6,994 | 0.1153 | 597 | 96.4 |
| Comp. Ex. E | 3,164 | 0.1704 | 599 | 95.5 |
| 20 | 5,079 | 0.1561 | 600 | 95.8 |
| 21 | 5,020 | 0.1476 | 599 | 95.9 |
| Comp. Ex. F | 3,728 | 0.1009 | 596 | 96.8 |
| 22 | 21,788 | 0.0792 | 647* | 94.1* |
| Comp. Ex. G | 1,440 | 0.1644 | 591 | 93.3 |
| 23 | 3,630 | 0.1068 | 599 | 96.0 |

*Performance data were estimated based on the observed conversion and selectivity at 600° C. The temperature required to achieve 70% conversion of ethylbenzene to products was calculated by assuming that a 1° C. increase in operating temperature would result in about a 0.6% increase in observed conversion and a 0.1% loss in selectivity.

This data shows the improved catalyst selectivity associated with restructuring the iron oxide. Selectivity gains were attained with relatively little or no corresponding loss in catalyst activity.

What is claimed is:

1. In a method of preparing iron oxide catalysts by mixing iron oxide particles with one or more promoters, forming a catalyst from the mixture, and calcining said catalyst, the improvement comprising restructuring the iron oxide particles prior to mixing the iron oxide particles with one or more promoters by a process comprising the steps of:

(a) contacting the iron oxide particles with a restructuring agent comprising a substance including an element selected from the group consisting of Mo, Cu, Ca, Zn, Mn, Sn, Ti, Bi, Co, Ce, W, Cr, Mg, and V, and (b) heating the iron oxide particles in contact with said restructuring agent of step a at least until iron oxide particles are formed which are essentially equant and have BET surface areas less than about 1.9 m²/gram, particle lengths of 0.3–3 μm and particle breadths of 0.2–2 μm.

2. The method of claim 1 wherein said restructuring agent is in the form of a member selected from the group consisting of monometallic oxidic salts, bimetallic oxidic salts, hydroxidic salts, simple salts, oxides, carbon containing compounds, hydrates, solvates and mixtures thereof.

3. The method of claim 2 wherein the restructuring agent is comprised of a member selected from the group consisting of compounds of molybdenum, copper, calcium, zinc, cobalt, and cerium.

4. The method of claim 2 wherein the restructuring agent is selected from the group consisting of ammonium dimolybdate, molybdenum trioxide, copper oxide, zinc oxide, calcium acetate, cobalt carbonate, and cerium (III) carbonate.

5. The method of claim 1 wherein step b is conducted at a temperature between about 600° C. and the melting point of the iron oxide particles.

6. The method of claim 5 wherein the heating step is conducted at a temperature between about 800° C. and 1100° C.

7. The method of claim 1 wherein said iron oxide particles are selected from the group consisting of hematite, lepidocrocite, goethite, maghemite, and magnetite.

8. The method of claim 1 wherein the restructuring agent comprises between about 0.5 and 6% wt (basis total weight of restructuring agent and iron oxide) of a member selected from the group consisting of ammonium dimolybdate, molybdenum trioxide, copper oxide, zinc oxide, calcium acetate, cobalt carbonate, and cerium (III) carbonate; and the heating step comprises heating said iron oxide particles in contact with said restructing agent to a temperature between about 800° and 1100° C. for about one hour.

* * * * *